United States Patent
O'Keefe et al.

(10) Patent No.: US 11,621,081 B1
(45) Date of Patent: Apr. 4, 2023

(54) SYSTEM FOR PREDICTING PATIENT HEALTH CONDITIONS

(71) Applicant: IQVIA Inc., Danbury, CT (US)

(72) Inventors: Michelle O'Keefe, Holland (PA); Lucas Glass, Devon, PA (US); Kristy Morgan, Chapel Hill, NC (US); Yunlong Wang, Malvern, PA (US); Yuliya Nigmatullina, London (GB); Yilian Yuan, North Wales, PA (US); Yong Cai, Bala Cynwyd, PA (US); Fan Zhang, Plymouth Meeting, PA (US); Chaitanya Alamuri, Morrisville, NC (US)

(73) Assignee: IQVIA Inc., Parsippany, NJ (US)

( * ) Notice: Subject to any disclaimer, the term of this patent is extended or adjusted under 35 U.S.C. 154(b) by 227 days.

(21) Appl. No.: 16/189,362

(22) Filed: Nov. 13, 2018

(51) Int. Cl.
*G16H 50/30* (2018.01)
*G06N 3/08* (2023.01)
*G16H 10/60* (2018.01)
*G06N 3/04* (2023.01)

(52) U.S. Cl.
CPC ........... *G16H 50/30* (2018.01); *G06N 3/0454* (2013.01); *G06N 3/08* (2013.01); *G16H 10/60* (2018.01)

(58) Field of Classification Search
CPC ... G06F 1/00–2221/2153; G16H 10/00–80/00; G06N 3/00–99/007
See application file for complete search history.

(56) References Cited

U.S. PATENT DOCUMENTS

| | | | |
|---|---|---|---|
| 6,538,029 B1 * | 3/2003 | Thompson | A61K 31/19 514/231.2 |
| 10,324,467 B1 * | 6/2019 | Abeloe | G10L 13/047 |
| 10,733,566 B1 * | 8/2020 | Chan | G06N 20/00 |

(Continued)

FOREIGN PATENT DOCUMENTS

| | | | | |
|---|---|---|---|---|
| JP | 6127160 B2 * | 5/2017 | | G06N 5/02 |
| WO | WO-0126026 A2 * | 4/2001 | | G06F 19/3418 |
| WO | WO-2018141061 A1 * | 8/2018 | | A61B 5/0022 |

OTHER PUBLICATIONS

Perry et al. "Assessment of the Feasibility of automated, real-time clinical decision support in the emergency department using electronic health record data," BMC Emergency Medicine (2018) 18:19. (Year: 2018).*

*Primary Examiner* — Jonathon A. Szumny
(74) *Attorney, Agent, or Firm* — Fish & Richardson P.C.

(57) ABSTRACT

Methods, systems, and apparatus, including computer programs encoded on a computer storage medium, for obtaining data for a set of patients that each have a certain condition. A first and second sequence of data is determined based on the obtained data. A scoring model is generated by processing the first and second sequence of data to train a neural network. The scoring model determines a confidence that an individual has the particular healthcare condition. Patient scoring data is provided to the scoring model to determine the confidence that the individual has the healthcare condition. A confidence score is received as an output of the scoring model in response to providing the patient scoring data. The confidence score represents a determined confidence that the individual has the healthcare condition. An indication that represents the confidence that the individual has the healthcare condition is provided based on the received confidence score.

22 Claims, 7 Drawing Sheets

(56) References Cited

U.S. PATENT DOCUMENTS

| | | | | |
|---|---|---|---|---|
| 2001/0023419 | A1* | 9/2001 | Lapointe | G16H 50/20 706/15 |
| 2005/0108052 | A1* | 5/2005 | Omaboe | G06Q 50/22 705/2 |
| 2007/0094048 | A1* | 4/2007 | Grichnik | G06Q 50/22 705/2 |
| 2007/0118399 | A1* | 5/2007 | Avinash | G16H 40/20 705/2 |
| 2008/0052122 | A1* | 2/2008 | Iliff | G06Q 50/24 705/2 |
| 2008/0183454 | A1* | 7/2008 | Barabasi | G16H 50/70 703/11 |
| 2009/0054740 | A1* | 2/2009 | Gudmundsson | G16H 50/70 600/300 |
| 2011/0099032 | A1* | 4/2011 | Miyasa | G16H 30/20 705/3 |
| 2012/0166212 | A1* | 6/2012 | Campbell | G16H 40/20 705/2 |
| 2012/0173280 | A1* | 7/2012 | Gustafson | G06Q 30/0631 705/3 |
| 2014/0316220 | A1* | 10/2014 | Sheldon | G16H 40/67 600/301 |
| 2015/0120319 | A1* | 4/2015 | Wilson | G16H 50/20 705/2 |
| 2015/0340032 | A1* | 11/2015 | Gruenstein | G06N 3/0472 704/232 |
| 2015/0352363 | A1* | 12/2015 | McIntyre | A61N 1/36067 607/45 |
| 2016/0012202 | A1* | 1/2016 | Hu | G16H 50/30 705/2 |
| 2017/0177796 | A1* | 6/2017 | Sellars | G16H 10/60 |
| 2018/0011980 | A1* | 1/2018 | Contu | G16H 50/20 |
| 2018/0060510 | A1* | 3/2018 | Baldauf | G16H 80/00 |
| 2018/0165418 | A1* | 6/2018 | Swartz | G16H 50/30 |
| 2019/0139643 | A1* | 5/2019 | Li | G06N 3/0454 |
| 2019/0155941 | A1* | 5/2019 | Bhide | G06N 5/046 |
| 2019/0172587 | A1* | 6/2019 | Park | G06F 17/18 |
| 2019/0237195 | A1* | 8/2019 | Berberian | G16H 50/50 |
| 2019/0380792 | A1* | 12/2019 | Poltaretskyi | G06N 3/0454 |
| 2020/0035335 | A1* | 1/2020 | Kivatinos | G06N 5/027 |
| 2020/0098476 | A1* | 3/2020 | Loscutoff | G06F 16/955 |
| 2020/0105419 | A1* | 4/2020 | Eickhoff | G16H 15/00 |
| 2020/0167914 | A1* | 5/2020 | Stamatoyannopoulos | G06N 20/00 |
| 2020/0394216 | A1* | 12/2020 | Tang | G06F 40/30 |

* cited by examiner

SYSTEM FOR PREDICTING PATIENT HEALTH CONDITIONS

FIELD

This specification relates to predictive computing systems.

BACKGROUND

As part of the healthcare process, physicians or other medical care providers may perform clinical trials, programs, and other activities to evaluate subject safety and efficacy of a pharmaceutical drug or other medical treatment option. The use of health-related trial programs can help to identify novel treatment options for improving overall patient health and reducing health system costs. A clinical trial or program can be a single research study or multiple research studies that prospectively assigns human participants/subjects or groups of human subjects to one or more health-related interventions to evaluate the effects on health outcomes.

SUMMARY

As part of the healthcare process, physicians or other medical care providers may perform trials, programs, and other activities to evaluate the efficacy of a particular pharmaceutical drug or other medical treatment option. Conducting health-related clinical trials can help to identify medical treatment options for improving overall patient health and reducing health system costs. Clinical trials and other controlled programs are generally conducted by investigators that use a particular geographic site location(s) to interact with study subjects. In some instances, a physician for a patient can be associated with a clinical trial and the physician can refer a patient as a candidate for participation in a trial based on a diagnosed condition of the patient. An investigator, a geographic site location, or both, can form an entity that executes a program. The effectiveness of a trial program can depend on a variety of factors, such as obtaining a sufficient number of subjects that are suitable for participation in a trial, the accuracy of diagnosed conditions for each patient or subject in the program, or certain types of conditions that may prospectively affect a subject. In some cases, factors that impact the effectiveness of a clinical trial can vary depending on the treatment options being evaluated and the criteria that are associated with the trial.

Based on the above context, this document describes a predictive computing system that uses specific computing rules or instructions (e.g., a unique algorithm) to predict or determine at least one condition that relates to the healthcare status of a patient (e.g., an undiagnosed medical condition). The condition can be a disease or medical ailment that presently affects the patient or that will prospectively affect the patient. The condition can indicate early detection of a disease or provide a basis for predicting progression of a current or future disease. In some instances, the predictive system may be configured to identify a misdiagnosis and determine a correct diagnosis with reference to a misdiagnosed condition. The predictive system trains an initial prediction model by processing sets of input data through layers of at least one neural network included at the system. The input data is uniquely structured in a sequenced format so as to enhance a feature engineering process of the predictive model. The specific instructions are learned by the predictive computing system when the neural networks process the inputs to generate the trained prediction model. The instructions can be adapted and refined for use at the trained model when new sets of input data are processed using the neural networks.

The system can identify past healthcare providers that treated a particular set of patients (e.g., diagnosed or at-risk patients). Referencing these past providers, the system uses the specific computing rules to more efficiently determine which provider(s) to target for treating a particular predicted condition of the patient. For example, the predictive system makes this determination in response to receiving query inputs that may specify certain diagnosis codes and other relevant disease risk factors associated with the patient. The system's trained prediction model processes the input data in accordance with the specific computing rules to generate a prediction result. The result can include an identified listing of clinical trials and site locations that execute trial programs evaluating medical options for treating the patient's predicted condition. Further, the result can also identify one or more providers that can be targeted for participation in any relevant clinical trials as well as providers (e.g., referral physicians) that are likely to refer patients to other physicians/investigators that are involved in a clinical trial. The providers/referral physicians may be targeted as having relevance to a clinical trial based on the healthcare or medical attributes of the patients that are treated by the providers.

One aspect of the subject matter described in this specification can be embodied in a computer-implemented method performed using a neural network comprising multiple neural network layers. The method includes: obtaining data for a set of patients that each have a particular healthcare condition; determining a first sequence of data based on the data for the set of patients, where the first sequence of data represents training data relating to healthcare transactions of the set of patients; and determining a second sequence of data based on the data for the set of patients, wherein the second sequence of data represents training data relating to healthcare providers of the set of patients.

The method further includes, generating a scoring model at least by processing the first and second sequence of data through one or more of the layers of the neural network to train the neural network, where the scoring model is configured to determine a confidence that an individual has the particular healthcare condition; and obtaining patient scoring data for determining the confidence that the individual has the particular healthcare condition using the scoring model, wherein the patient scoring data is not included in the data for the set of patients.

The method also includes, providing the patient scoring data to the scoring model to determine the confidence that the individual has the particular healthcare condition; in response to providing the patient scoring data to the scoring model, receiving a confidence score as an output of the scoring model, wherein the confidence score represents a determined confidence that the individual has the healthcare condition; and providing, based on the received confidence score, an indication that represents the confidence that the individual has the healthcare condition.

These and other implementations can each optionally include one or more of the following features. For example, in some implementations, the method further includes: determining, by the scoring model, the confidence score in response to processing the obtained patient scoring data through the one or more layers of the neural network.

In some implementations, generating the scoring model includes: providing the first and second sequence of data as inputs to a layer of the neural network; and training the neural network in response to processing the first and second sequence of data through the layer of the neural network.

In some implementations, the scoring model is a trained neural network model configured to identify latent variables in the obtained patient scoring data. In some implementations, the scoring model determines the confidence that the individual has the particular healthcare condition based on training inferences computed when the neural network is trained using at least the first and second sequence of data.

In some implementations, the method further includes: determining a third sequence of data based on the data for the set of patients, wherein the third sequence of data represents training data relating to patient specific information; and generating the scoring model at least by processing the first, second, and third sequence of data through the one or more layers of the neural network.

In some implementations, the first sequence of data includes data describing procedures, products, or diagnoses and is formatted for processing through the one or more layers of the neural network; the second sequence of data includes data describing healthcare provider specialties and is formatted for processing through the one or more layers of the neural network; and the third sequence of data includes data describing patient demographics and is formatted for processing through the one or more layers of the neural network.

In some implementations, the method further includes: encoding, as a vector, at least one of the procedure, the product, or the diagnosis in the first sequence of data; and obtaining an encoding rule associated with the vector by using a second neural network to learn inferences based on analysis of at least one vector dataset that includes the vector.

In some implementations, the determined confidence that the individual has the particular healthcare condition corresponds to: (i) a current healthcare condition or (ii) a prospective healthcare condition; and the indication at least one of: (ii) identifies a particular disease that currently affects the individual, or (ii) identifies whether the individual is at risk for contracting a particular disease.

In some implementations, the individual is a patient and providing the indication includes: identifying a healthcare provider for treating the particular disease; linking data for the patient to data for the healthcare provider; and providing the indication using linked data for the patient and the healthcare provider.

In some implementations, the individual is a patient and providing the indication includes: identifying a clinical trial that evaluates drug options for treating the particular disease; linking data for the patient to data for the clinical trial; and providing the indication using linked data for the patient and the clinical trial.

In some implementations, providing the indication includes: identifying a healthcare provider for treating the particular disease. In some implementations, obtaining the data for the set of patients includes: obtaining data for a subset of patients that each have the same healthcare condition.

Other implementations of this and other aspects include corresponding systems, apparatus, and computer programs, configured to perform the actions of the methods, encoded on computer storage devices. A computing system of one or more computers or hardware circuits can be so configured by virtue of software, firmware, hardware, or a combination of them installed on the system that in operation cause the system to perform the actions. One or more computer programs can be so configured by virtue of having instructions that, when executed by data processing apparatus, cause the apparatus to perform the actions.

The subject matter described in this specification can be implemented to realize one or more of the following advantages. The described techniques provide a scalable predictive computing system that is configured to quickly and efficiently analyze data describing a variety of indications. Based on the analysis, the predictive system accurately infers a particular disease or medical condition affecting a subject or patient. The system also allows for fast identification of healthcare providers (HCPs) and patients that are associated with any selected disease. Another advantage is the speed of the identification can be accomplished using specific computing-rules that are automatically learned by the system based on machine learning. For example, the system can learn a set of rules for identifying the various types of health related conditions noted above (e.g., undiagnosed, misdiagnosed, early detection, disease progression, etc.) or clinical trials using one or more neural networks. The system can then adapt or enhance the rules in response to analyzing new datasets using the neural networks.

In this manner, the described techniques enable configuring a predictive system as a fully data driven model that requires very little manual clinical input to obtain accurate prediction results. The results can identify certain undiagnosed or health related conditions as well as referral physicians and investigators that are involved in clinical trials for treating those conditions. The predictive system can adapt to perform the same analytical evaluation on data for different diseases or types of conditions. The system can also use the rules (e.g., algorithms) to assess the eligibility of the affected patients for participating in a clinical trial that evaluates medical options for treating the patients' predicted health conditions.

The details of one or more implementations of the subject matter described in this specification are set forth in the accompanying drawings and the description below. Other potential features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Predictive modeling can require substantial time and effort, particularly for the feature engineering process. During this process, data scientists leverage their domain knowledge to create features needed to perform the predictive analysis. Earlier approaches for evaluating a patient population with a specific disease included evaluating features, also known as predictors, or risk factors on a case-by-case basis.

Typically, data scientists do not immediately create the most optimal features that can best predict the output variable, and initial features may require many revisions and frequent updates. In some instances, feature engineering is accompanied with trial and error processes, which can be time consuming and costly. When these antiquated modeling processes are used to evaluate or confirm subject eligibility for participation in clinical trials, they often yield inaccurate and undesired predictive outcomes. For example, such processes can result in screening failure rates that are greater than 80% for certain indications, which lead to missed enrollment targets for clinical trials.

In this context, techniques are described for a predictive computing system configured to accurately detect or predict one or more undiagnosed medical conditions that affects a patient. The system can also predict prospective conditions that are likely to affect the patient based on one or more types of healthcare data analyzed by the system. The described computing system substantially streamlines the feature engineering process. For example, the techniques involve use of specific-computing rules that enable the predictive system to actively learn from current and future datasets.

The system is configured to uniquely format the datasets for processing through layers of one or more neural networks that are included in the system. Respective sets of healthcare transaction data, as well as patient demographic data, are obtained and formatted for processing at the system to train an initial prediction model using the one or more neural networks. Sets of scoring data are formatted and processed to validate accuracy of scoring indications generated by the initial scoring model. The trained model is then used to generate prediction indications for sets of patients. These indications represent predicted diseases or other medical conditions that are presently affecting, or will affect, individual patients in the set of patients.

Figure 1:
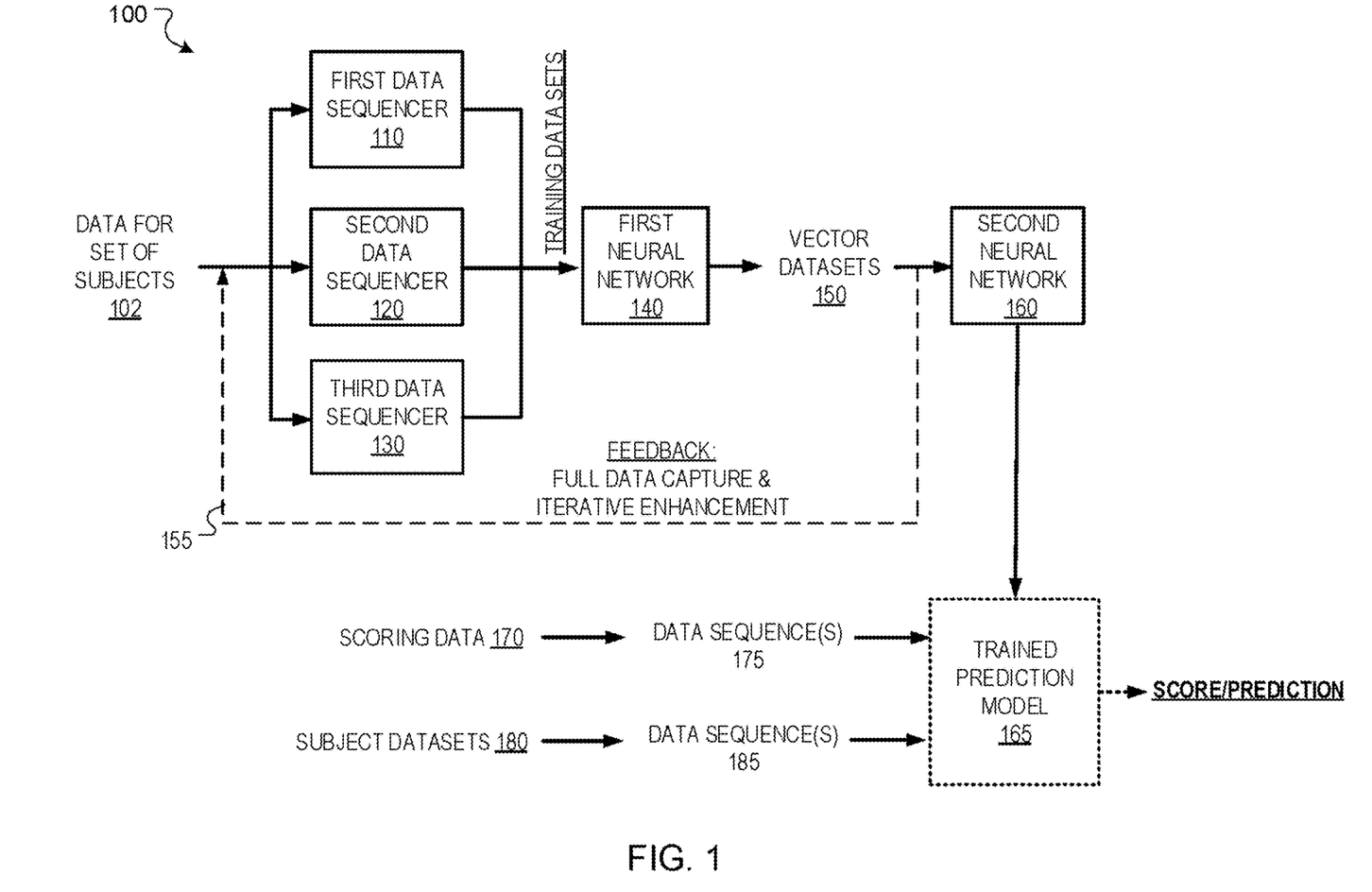
FIG. 1 shows a block diagram of an example computing system for detecting undiagnosed conditions.

FIG. 1 shows a block diagram of an example computing system 100 for detecting undiagnosed conditions. System 100 can be a predictive computing system configured to process sets of input data to train a scoring model used to predict an undiagnosed condition that affects a patient. In general, system 100 obtains or receives data 102 for a set of subjects that each have a particular healthcare condition. The data 102 is obtained for processing at system 100 and can include a variety of different types of data relating to various healthcare activities. For example, the data may describe health and medical attributes for a large set of patients or subjects or may describe sponsorship and execution details for a set of clinical trials. In some cases, data 102 includes multiple respective datasets of healthcare transaction information and multiple respective datasets of demographic information for individual patients.

The healthcare transaction information can be obtained from data describing interactions between physicians and patients, data derived from a subject's physical or electronic medical records (EMR), data derived from prescription records/medical claims ("Rx/Dx data"), data relating to prescriptions or treatment options used by a patient or subject, or from other data sources relating to healthcare transactions and healthcare activities. The demographic information may include a patient identification number, a subject's age, a subject's gender and/or preferred pronoun, a subject's geographic region or address location, as well as other identifying data about a person. As used in this document, a patient may be referred to as a subject, and vice versa. In some implementations, a subject may be a candidate for participation in a clinical trial, a participant in a clinical trial, or an existing patient of a healthcare provider that may be identified for participation in a clinical trial.

System 100 generally includes data sequencers 110, 120, 130, a first neural network 140, and a second neural network 160. Sequencers 110, 120, 130 are each configured to: i) receive a set of data relating to healthcare transactions for a patient, ii) analyze the data to identify a particular group of parameters for each event, and iii) determine an arrangement of the data for each event based on corresponding parameter values for the event and in accordance with an example sequencing instruction. The sequencers 110, 120, and 130 can also generate an example data structure that represents a sequence of data. The data structure can arrange sets of healthcare events in a time-ordered sequence as specified by the sequencing instruction.

Sequences of data can represent training data used to train at least one neural network of system 100. For example, a training data set can define a group of diagnosed patients that each have a particular disease being evaluated. Multiple respective training data sets can be generated such that neural networks of system 100 are trained using an expansive dataset of information that includes all available data for healthcare events involving a given set of patients. The neural networks process the training data to identify, infer, or otherwise determine the most important features (e.g., lab values, diagnosis codes, EMR notes, etc.) for predicting an undiagnosed condition that affects a patient. In some implementations, the neural networks identify the most important features based on a machine learning algorithm that determines commonalities (e.g., health related commonalities) across patients using available data in the training data set.

Sequencer 110 is configured to determine a first sequence using information included in the data 102 for the set of patients. This first sequence of data represents training data that describes details about healthcare transactions for the set of patients. For example, the first sequence of data includes information describing medical procedures (e.g., Prc A, B, or C), pharmaceutical drugs or other medical treatment products (e.g., Prod A, B, or C), or medical diagnoses (e.g., Diag A, B, or C). The training data set represented by the first sequence of data is provided to the neural network 140 for processing through one or more layers of the neural network 140. In some implementations, the first data sequencer 110 is a procedure product diagnosis (PPD) data sequencer that generates a PPD training data set. Neural network 140 processes the training data provided as an output of the PPD data sequencer 110 to generate a PPD vector dataset 150.

Sequencer 120 is configured to determine a second sequence of data using information included in the data 102. This second sequence of data represents training data that describes details about physicians or providers who engage in healthcare transactions to provide treatment to a set of patients or to prescribe drugs for the set of patients. For example, the second sequence of data includes information describing a variety of medical provider specialties, such as family medicine (e.g., FM), endocrinology (e.g., END), or orthopedic surgery (e.g., OS). The training data set represented by the second sequence of data is also provided to the neural network 140 for processing through one or more layers of the neural network 140. In some implementations, the second data sequencer 120 is a healthcare provider (HCP) specialty data sequencer that generates an HCP specialty training data set. Neural network 140 processes the training data provided as an output of the HCP specialty data sequencer 120 to generate a HCP specialty vector dataset 150.

Sequencer 130 is configured to determine a third sequence of data using information included in the data 102 for the set of patients. This third sequence of data represents training data that describes details about patient demographics. In some cases, the details about patient demographics are described in the third sequence of data with reference to PPD parameters and HCP specialty parameters for healthcare transactions involving a particular patient and one or more treating physicians. For example, the third sequence of data can include information describing an identification number for a patient, an age of the patient, or the patient's gender. Various other attributes relating to patient demographic information can be also described in the third sequence of data.

The training data set represented by the third sequence of data is also provided to the neural network 140 for processing through one or more layers of the neural network. In some implementations, the third data sequencer 130 is a hybrid data sequencer that generates a training data set using demographic data as well as various other information about healthcare transactions involving patients identified in data 102. For example, this other information can include diagnosis codes and disease risk factors that were identified by a treating physician during an example healthcare transaction to evaluate the patient's medical status. In some implementations, training data generated by the hybrid data sequencer 130 includes parameters relating to PPD information, HCP specialty information, and patient demographic information. Neural network 140 processes the training data provided as an output of the third data sequencer 130 to generate a hybrid vector dataset 150. Each vector dataset 150 is provided to, and processed at, a second neural network 160 to generate a prediction model 165.

In processing the respective data sequences generated by data sequencers 110, 120, 130, second neural network 160 (e.g., a deep neural network) provides an additional neural network that is trained to map each unique type of the medical services (e.g., the unique parameter values in an example PPD or HCP specialty sequence) as a vector that is the latent representation of the service type as understood by an example neural network or deep neural network.

As discussed above, input data 102 for a set of subjects 102 is uniquely structured in a sequenced format, e.g., using data sequencers 110, 120, 130, so as to enhance a feature engineering process of the predictive model. In some implementations, parameter values and other detailed information associated with the procedure, the product, and the diagnosis in an example PPD sequence are encoded as a vector based on an example encoding rule. The encoding rule is obtained based on learned inferences that are determined when the neural network 140 (e.g., a deep neural network) processes one or more of the training datasets generated at least by PPD data sequencer 110.

For example, each data item in the PPD sequence can be encoded as a vector and the encoding rule can be learned by the deep neural network itself using the training data set that corresponds to the PPD sequence. This encoding function of the neural network can correspond to a word embedding function that serves to further enhance the prediction accuracy predictions about undiagnosed conditions that are generated by the system 100.

A prediction accuracy of the model is evaluated using scoring data 170. For example, the scoring data 170 can represent a curated dataset for which all diseases and indications are known. The trained prediction model 165 can receive data sequences 175 that are derived from scoring data 170 and a user can input a test query to obtain a prediction score. The prediction model 165 can process the test query against the scoring data 170 to generate prediction scores for evaluating the accuracy of the prediction model 165. In other implementations, once the accuracy of the model has reached a threshold accuracy, data sequencers 110, 120, and 130 can process raw unstructured data for subject datasets 180 to generate data sequences 185 that are submitted to the trained prediction model 165 to generate a prediction score for a real-world patient or set of patients.

The prediction model 165 is configured to automatically identify or detect, as well as analyze various risk factors and diagnosis codes that are present in each of the respective data sequences 190 to identify undiagnosed/at-risk patients. In some implementations, the prediction model 165 is configured to identify a current undiagnosed medical condition for any desired indications or diseases. In other implementations, the prediction model 165 is configured to identify a future medical condition for any desired indications or diseases that may otherwise go undiagnosed in a set of at-risk patients.

The system 100 uses one or more machine learning processes that are capable of learning from new data; based on this, the prediction model 165 is configured to continually increase its prediction accuracy. For example, the prediction model 165 can continually increase its prediction accuracy as additional patient datasets become available for sequencing (using the data sequencers) subsequent processing at the neural networks 140, 160 that may form the prediction model 165.

System 100 can be configured to include a feedback loop 155 where encoded vector outputs may be fed back as inputs to system 100 to ensure full capture of discrete parameters in a set of information processed at the data sequencers. In some implementations, the system 100 is configured to iteratively enhance its prediction capabilities by using the feedback loop 155 to reevaluate vector outputs to, e.g., detect commonalities that exist among a more granular set of data. In some case, the system 100 can use the data sequencers 110, 120, 130 to jointly process various claims level data with reduced computation cost and better accuracy relative to conventional systems. In general, an example training process of system 100 can be based on the feedback loop 155, in which embedded vectors (outputs) are feedback to the system 100 as inputs to the system that are then analyzed to iteratively enhance the accuracy of the parameters generated by the system 100.

Figure 2:
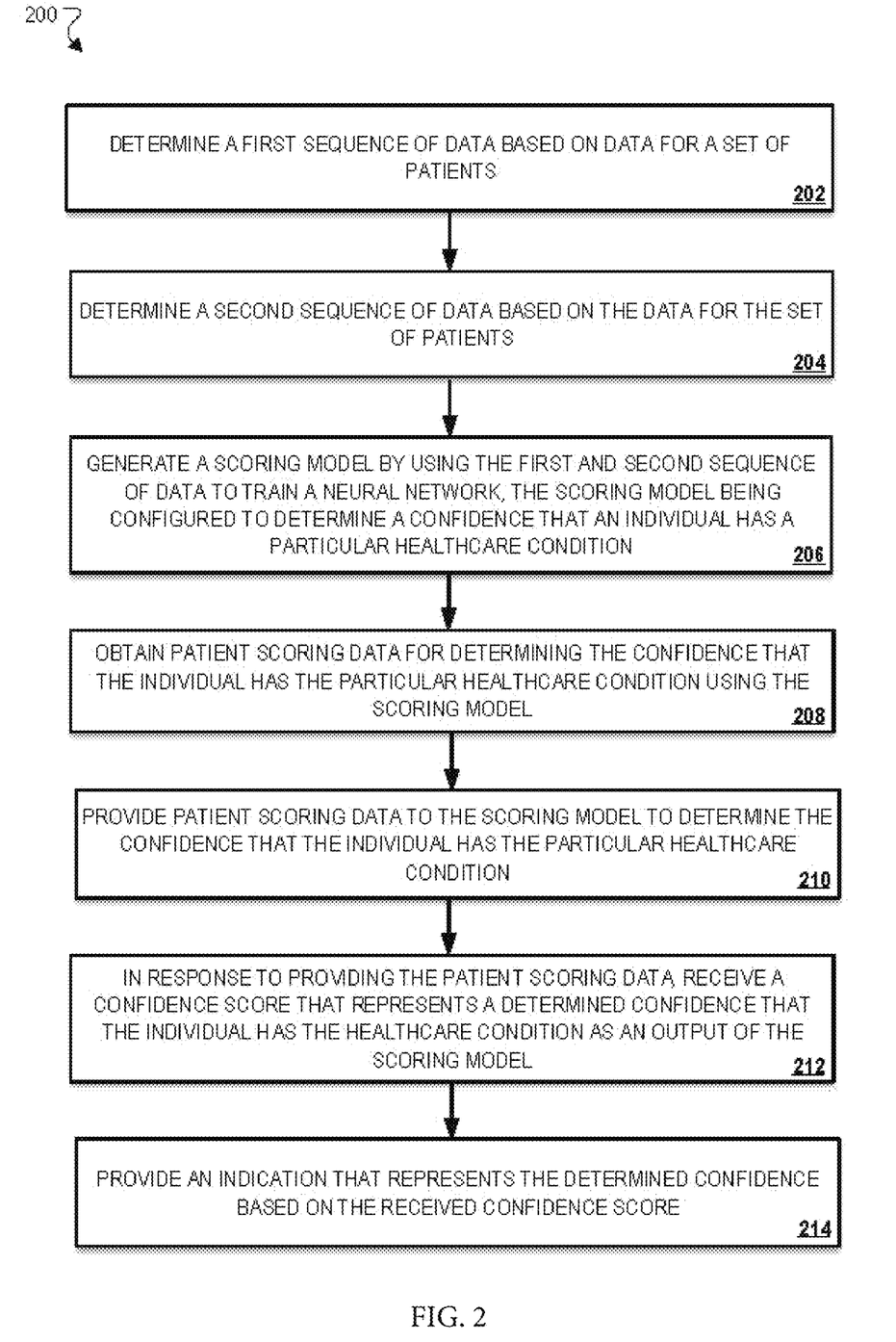
FIG. 2 shows an example process for detecting undiagnosed conditions of a subject.

FIG. 2 shows an example process 200 for detecting undiagnosed conditions of a subject. Process 200 can be implemented using one or more computing elements of system 100 described above as well as other components and instructions described in this document.

Referring now to process 200, system 100 obtains data for a set of patients that each have a particular healthcare condition. For example, the condition may be any known medical condition such as hypertension, a particular type of cancer, or diabetes. Sequencer 110 determines a first sequence of data based on the data for the set of patients (202). The first sequence of data represents training data relating to healthcare transactions of the set of patients. For example, the first sequence of data includes information describing medical procedures, pharmaceutical drugs or other medical treatment products, or diagnoses. The first sequence of data is formatted in a time-ordered or sequenced listing that represents a set of training data to be processed through layers of a neural network included at the system 100.

Sequencer 120 determines a second sequence of data based on the data for the set of patients (204). The second sequence of data represents training data relating to healthcare providers of the set of patients. For example, the second sequence of data can include data describing healthcare provider specialties and represents training data formatted for processing through the one or more layers of neural network 140. In some implementations, sequencer 130 determines a third sequence of data based on the data for the set of patients. The third sequence of data represents training data describing patient specific information, such as an age of a patient, a patient's gender, or other information related to patient demographics.

The system 100 generates a prediction model 165 in part by processing the first and second sequences of data through one or more of the layers of at least a first neural network 140 (206). The first and second sequences of data are processed to train at least the neural network 140, the neural network 160, or both. In addition to the first and second sequences of data, system 100 can also obtain a third sequence of data, where each of the first, second, and third sequences of data are processed to train the neural networks of system 100. For example, system 100 can generate the prediction model 165 at least by processing the first, second, and third sequence of data (e.g., training data sets) through the one or more layers of neural networks 140. In some implementations, generating the prediction model includes providing at least the first and second sequences of data as inputs to a layer of the neural network 140 and training the neural network 140 in response to processing the first and second sequences of data through the layer of the neural network 140.

The prediction model 165 is configured to determine a confidence that an individual has the particular healthcare condition. In some implementations, the model is configured to determine a confidence that the individual has the condition and that the condition has not yet been diagnosed. Hence, scoring model 165 is configured to infer, detect, or otherwise predict one or more undiagnosed conditions that are presently affecting a patient. In other implementations, the system 100 is configured to predict one or more future healthcare conditions that will affect the individual based on analysis of prior healthcare data associated with the individual. As discussed in more detail below, the prediction model 165 can generate a confidence score (e.g., a numerical score) that is associated with an indication about an undiagnosed condition. Hence, the prediction model 165 can be a scoring model 165 that generates an output score to indicate an undiagnosed condition.

The system 100 obtains patient scoring data 170 and uses at least one data sequencer 110, 120, 130 to generate data sequences 175 for determining the confidence that the individual has the particular healthcare condition using the scoring model (208). In some implementations, the scoring model 165 determines the confidence score in response to processing the obtained patient scoring data 170 through the one or more layers of neural network 140. In some cases, the prediction model 165 is a trained neural network model that is configured to identify latent variables in any dataset that is input for processing to the system 100, such as the obtained patient scoring data or subject datasets 180.

In general, the patient scoring data is not included in the data for the set of patients. The system 100 provides the data sequences 175 derived from patient scoring data 170 to the scoring model 165 to determine the confidence that the individual has the particular healthcare condition (210). As discussed above, a prediction accuracy of the model is evaluated using scoring data 170. In some implementations, the scoring data 170 is provided to the scoring model as discrete sets of sequenced data 175. For example, at least one of sequencers 110, 120, or 130 can be used to generate a sequence listing of data entries that correspond to the scoring data 170. The system 100 receives a confidence score as an output of the scoring model 165 in response to providing the patient scoring data 170 to the scoring model. The confidence score represents a determined confidence that the individual has the healthcare condition (212). In some implementations, an initial confidence score is received that is used to evaluate the accuracy of the trained prediction model 165 using data sequences 175 derived from scoring data 170.

In addition to scoring data 170, the system 100 obtains subject datasets 180 and generates data sequences 185 for determining the confidence that the individual has the particular healthcare condition using the scoring model 165. The system 100 uses data sequences 185 to obtain a confidence score that represents a determined confidence that a patient or subject has a particular healthcare condition. The scoring model 165 determines the confidence that the individual has the healthcare condition based on training inferences computed when the neural network is trained using at least the first and second sequence of data discussed above. The system 100 uses the prediction model 165 to provide an indication that represents the confidence that the individual has the healthcare condition (214). The system 100 provides the indication based on the received confidence score generated by the prediction model 165.

For example, a confidence score is received by the system 100 in response to query input submitted for processing using the scoring model 165. The query input may ask whether a particular patient (Patient: John/Jane Doe) has any current undiagnosed medical conditions, misdiagnosed conditions, or symptoms indicating early detection of a disease. Similarly, the query input may also ask whether subject John/Jane Doe will have particular medical conditions in the future, which may correspond to early detection of a disease or progression of a current condition. The scoring model 165 can generate a confidence score of 0.8 in response to processing the query. In some cases, the query input is used to identify one or more clinical trials for which the patient is likely to be enrolled as a subject in the trial. For example, system 100 can be used to identify clinical trial sites as well as a set of patients or subjects that are eligible to participate in the clinical trials.

Providing the indication can include identifying a healthcare provider for treating the particular disease or medical condition that is associated with a health related condition of a patient, such as an undiagnosed medical condition. In some implementations, the indication includes the determined confidence score and an example data structure that links information (e.g., medical information) for the patient to an example computer system managed by an identified healthcare provider or physician. The physician may have a provider specialty that is appropriate for treating the undiagnosed condition that affects the patient or subject.

Providing the indication can also include identifying a clinical trial that evaluates drug options for treating the particular disease or medical condition that is associated with the health related condition affecting, or that will affect, the patient.

In other implementations, system 100 can receive a query that specifies a given indication or disease, such as lung cancer. Based on inferences learned, for example, by analyzing data derived from a patient's medical records or Dx/Rx data, the scoring model 165 predicts a probability of whether a patient has the specified disease or will have the disease in the future. For example, using input sequences derived from the patient's medical record, system 100 generates predictions (e.g., a confidence score) that indicates a likelihood or probability that the patient will be diagnosed with the specified disease in the future. In some cases, the predicted score is provided to the patient's doctor or healthcare provider or other persons that are permitted to view the predicted result.

In some cases, the prediction model 165 predicts whether a patient has a health related condition that has developed or progressed to particular disease of interest (DOI). In response to generating this prediction, the system 100 can be configured to apply certain business rules and knowledge of clinical processes to define relevant medical specialties and physicians that are particularly suited for treating the DOI. In some implementations, the system 100 is configured to associate, join, or otherwise link data identifying the patients' predicted condition(s) to information describing the relevant medical specialties and corresponding physicians that have the relevant expertise for treating the DOI.

Figure 3A:
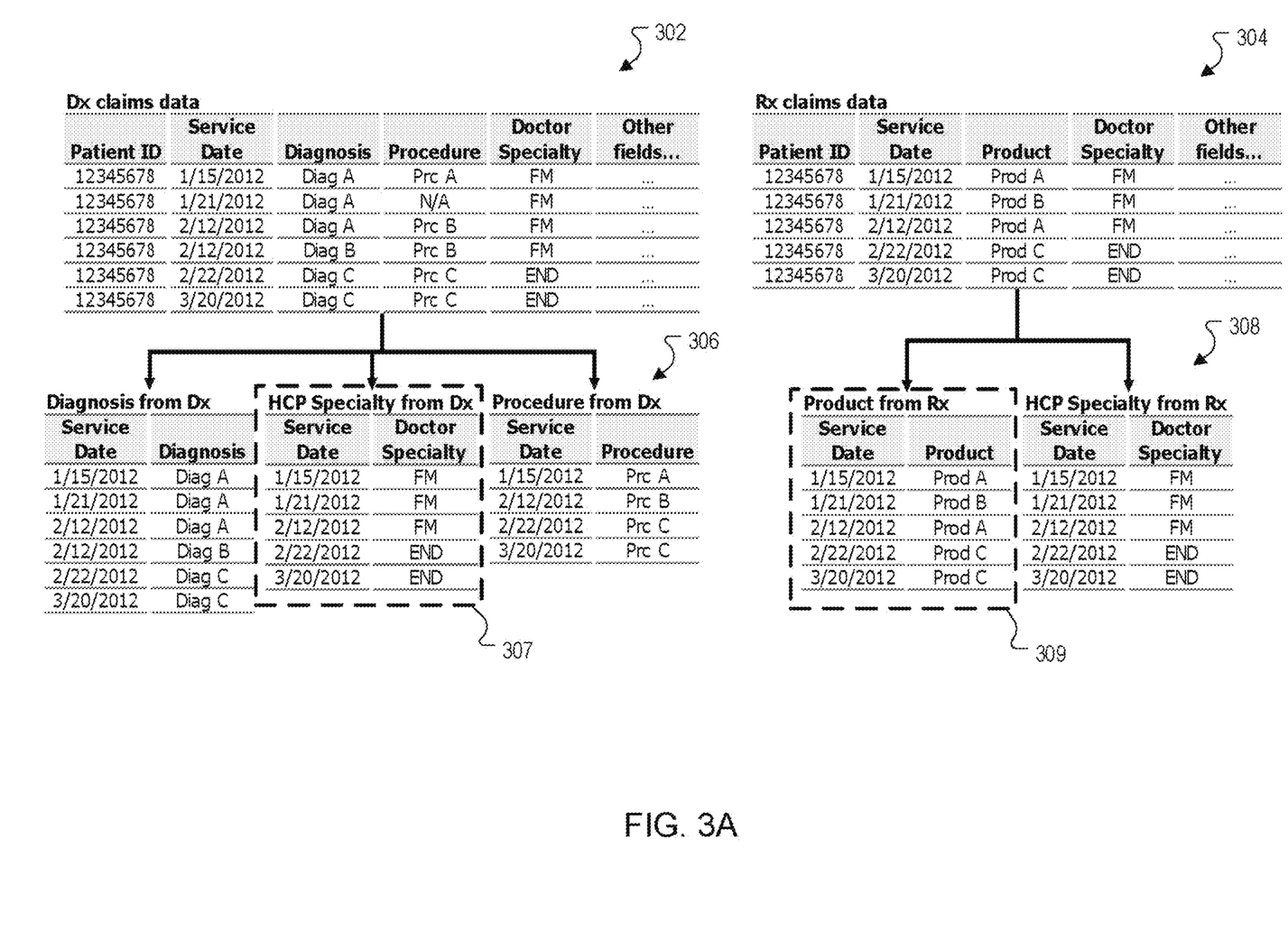
FIG. 3A-3C each show example datasets that are processed to detect one or more undiagnosed conditions of a subject.
Figure 3B:
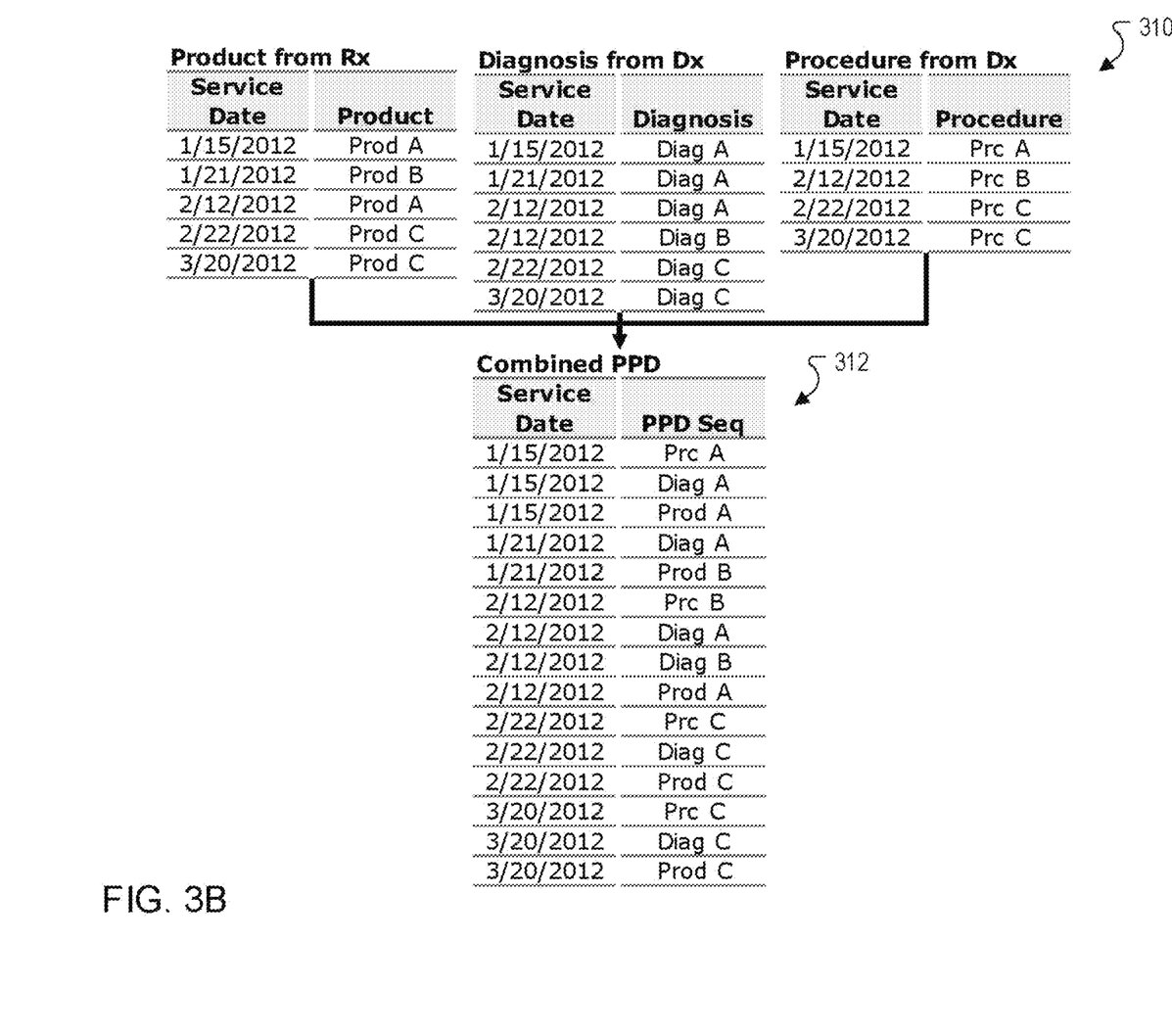
Figure 3C:
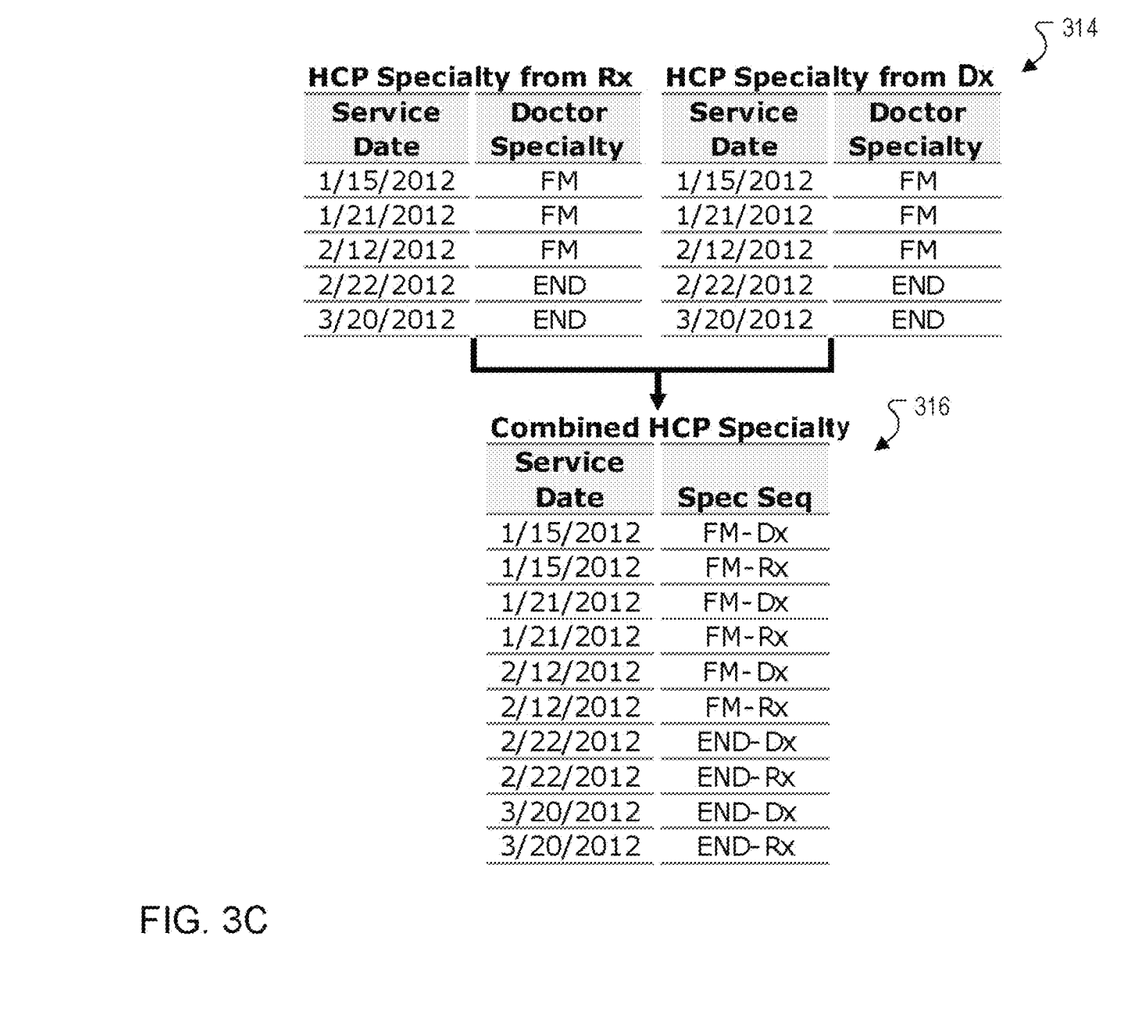

FIGS. 3A, 3B, and 3C each show example datasets that are processed to detect one or more undiagnosed conditions of a subject. As discussed in more detail below, a portion of these datasets can represent raw unstructured data (e.g., longitudinal patient data) that is input to one or more of data sequencers 110, 120, 130 to generate a vector dataset for training a neural network.

FIG. 3A includes Dx dataset 302 and Rx dataset 304. Dx dataset 302 represents claims data for healthcare transactions relating to a medical diagnosis, a medical procedure associated with the medical diagnosis, and a doctor or physician that is associated with the medical diagnosis, the medical procedure, or both. Rx dataset 304 represents claims data for healthcare transactions relating to a drug product and a physician that is associated with the drug product, such as a prescribing physician.

Datasets 302, 304 can each correspond to raw unstructured data for an individual patient, or multiple patients. At least one of datasets 302, 304 are input to data sequencer 110 to generate an example first sequence of data that includes information describing medical procedures (e.g., Prc A, B, or C), pharmaceutical drugs or other medical treatment products (e.g., Prod A, B, or C), or medical diagnoses (e.g., Diag A, B, or C) for the patient. Likewise, at least one of datasets 302, 304 are input to data sequencer 120 to generate an example second sequence of data that includes information describing a variety of medical provider specialties, such as family medicine (e.g., FM), endocrinology (e.g., END), or orthopedic surgery (e.g., OS) relating to treatment received by the patient.

In some implementations, to generate an example PPD sequence of data, data sequencer 110 can arrange, format, or otherwise organize information included in the Dx dataset 302 to generate an example data structure 306. Data structure 306 includes discrete listings for medical diagnosis, physician specialty, and medical procedures, where each listing is arranged in order of service date. For example, data sequencer 110 can extract each information item, e.g., for a diagnosis, a procedure, or a physician specialty, from dataset 302 and associate the extracted item with a corresponding data of service that indicates when a healthcare transaction involving that item occurred. Data sequencer 120 may perform the same or substantially similar processes to generate an example HCP specialty sequence of data.

Similarly, to generate the example PPD sequence of data, data sequencer 110 can arrange, format, or otherwise organize information included in the Rx dataset 304 to generate an example data structure 308. Data structure 308 includes discrete listings for medical treatment products and physician specialties associated with the medical treatment product, where each listing is arranged in order of service date. For example, data sequencer 110 can extract each information item, e.g., for a drug product or the specialty of a physician that prescribed the drug product, from dataset 302 and associate the extracted item with a corresponding data of service that indicates when a healthcare transaction involving that item occurred. Data sequencer 120 may perform the same or substantially similar processes to generate an example HCP specialty sequence of data.

In some implementations, to generate the PPD sequence of data, the data sequencer 110 removes or discards physician specialty information in discrete listing 307 from data structure 306, extracts the medical treatment product information in discrete listing 309 from data structure 308, and combines the product information in discrete listing 309 with the procedure and diagnosis information in the other discrete listings of data structure 306 to form a modified data structure 310 as shown at FIG. 3B. The data sequencer 110 processes the modified data structure 310 to generate an example PPD training data set represented by a PPD data sequence 312 shown at FIG. 3B. The PPD training data set is provided to the neural networks of system 100 to train the neural network to predict an undiagnosed condition in the patient.

In a related implementation, to generate the HCP specialty sequence of data, the data sequencer 120 removes or discards the medical treatment product information in discrete listing 309 from data structure 308, extracts the physician specialty information in discrete listing 307 from data structure 306, and combines the physician specialty information in discrete listing 307 with the physician specialty information in at least one other discrete listing in data structure 308 to form a modified data structure 314 as shown at FIG. 3C. The data sequencer 120 processes the modified data structure 314 to generate an example HCP specialty training data set represented by a HCP specialty data sequence 316 shown at FIG. 3C. The HCP specialty training data set is also provided to the neural networks of system 100 to train the neural networks to predict an undiagnosed condition in the patient.

Figure 4:
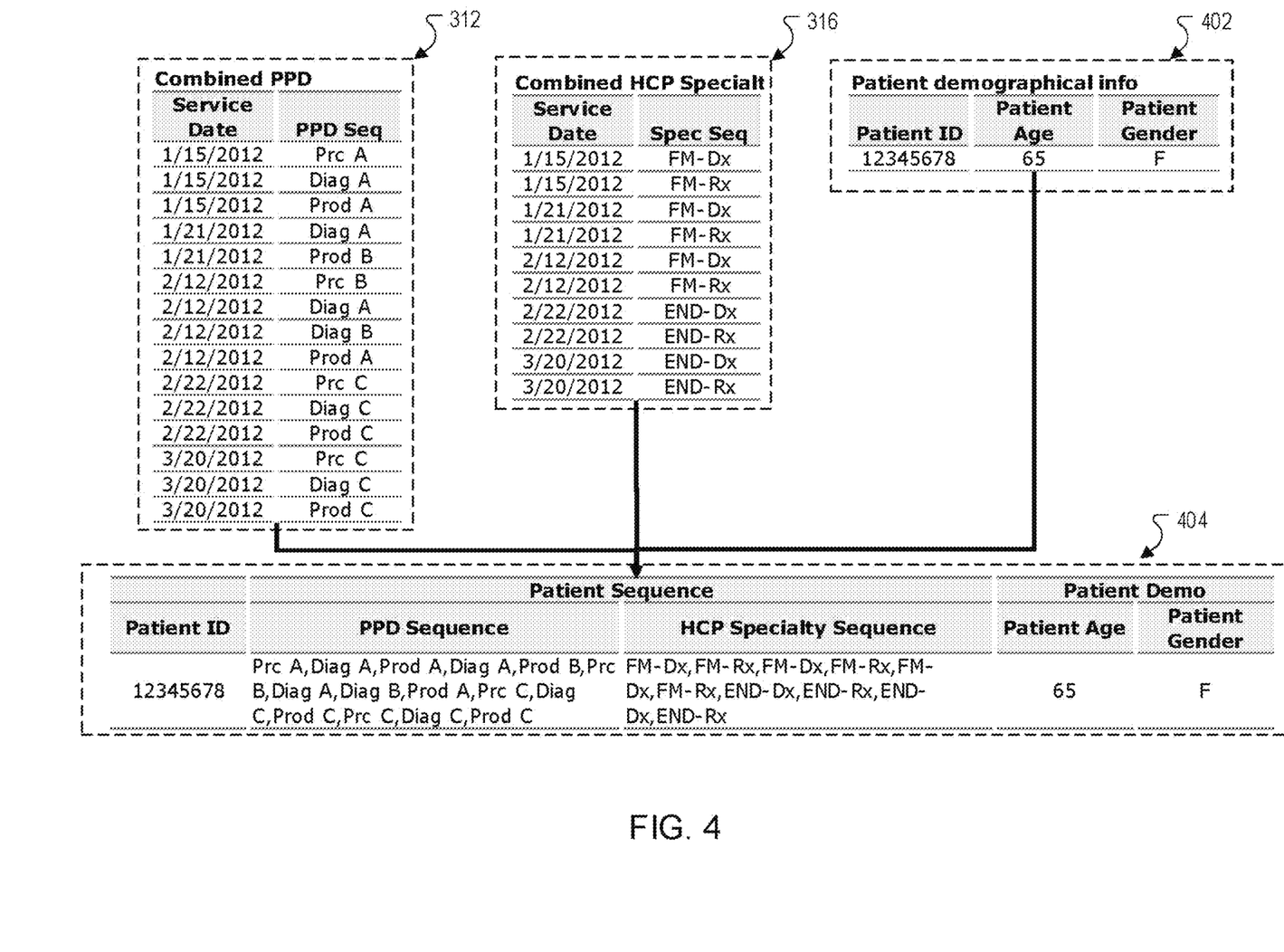
FIG. 4 shows example data sequences that can be processed to detect one or more undiagnosed conditions of a subject.

FIG. 4 shows example data sequences that are processed to detect one or more undiagnosed conditions of a subject. For example, PPD data sequence 312, HCP specialty data sequence 316, and demographic data sequence 402 can combine to form an example composite training data set 404. Demographic data sequence 402 can be obtained from one or more of Dx dataset 302, Rx dataset 304, or other types of data included in data 102. Further, demographic data sequence 402 can be obtained from these data sources at least based on data processing and extraction functions performed on these sources using data sequencer 130.

Training data 404 is provided to train the neural networks of system 100 to identify certain important features for detecting one or more undiagnosed conditions in a patient. For example, the neural networks can use one or more machine learning (ML) algorithms to process discrete parameters included in training data 404. Using the ML algorithms, the neural networks can determines commonalities (e.g., health related commonalities) across one or multiple patients using available data in a respective set of training data 404 for each individual patient.

Figure 5:
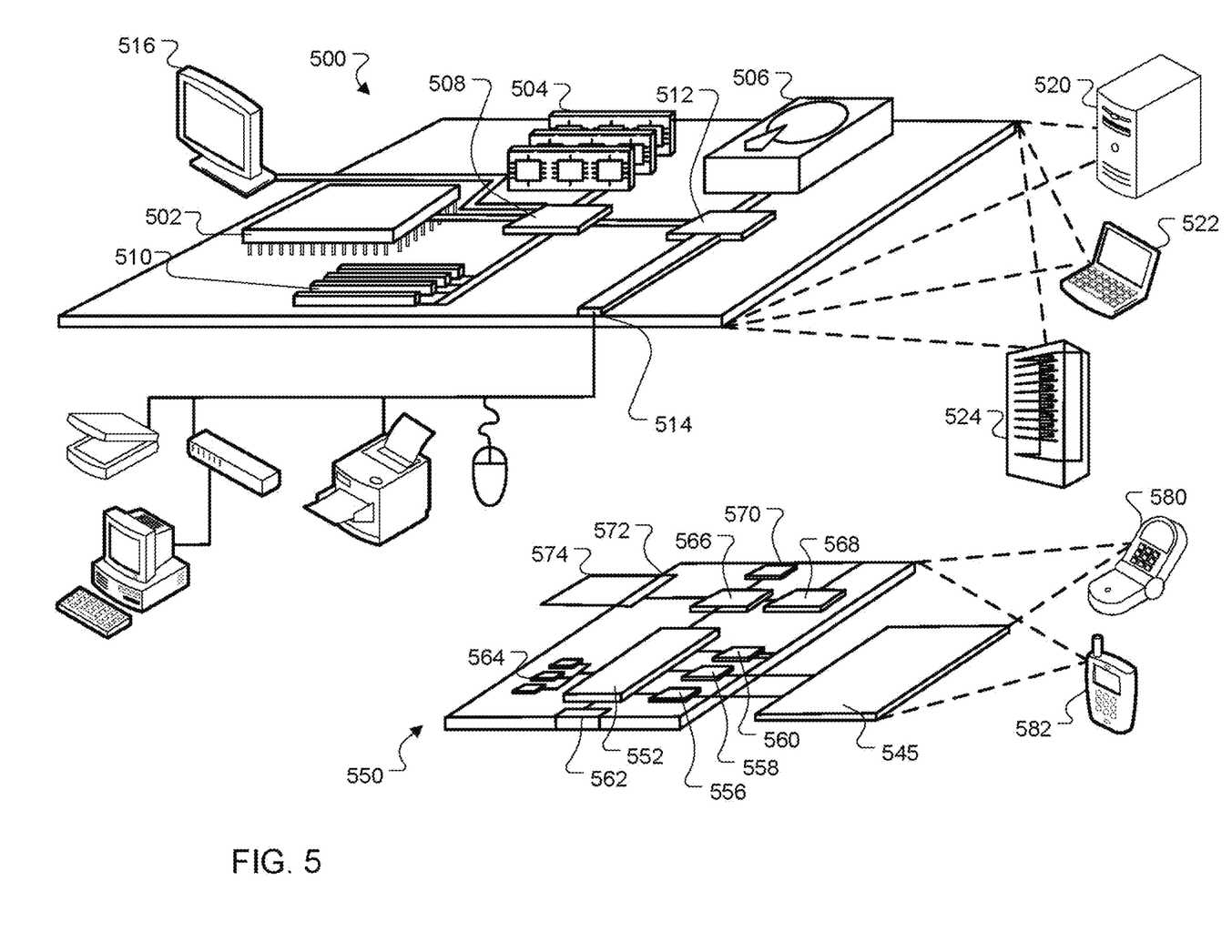
FIG. 5 shows a block diagram of a computing system that can be used in connection with methods described in this document.

FIG. 5 is a block diagram of computing devices 500, 550 that may be used to implement the systems and methods described in this document, as either a client or as a server or multiple servers. Computing device 500 is intended to represent various forms of digital computers, such as laptops, desktops, workstations, personal digital assistants, servers, blade servers, mainframes, and other appropriate computers. Computing device 550 is intended to represent various forms of mobile devices, such as personal digital assistants, cellular telephones, smartphones, smartwatches, head-worn devices, and other similar computing devices. The components shown here, their connections and relationships, and their functions, are meant to be exemplary only, and are not meant to limit implementations described and/or claimed in this document.

Computing device 500 includes a processor 502, memory 504, a storage device 506, a high-speed interface 508 connecting to memory 504 and high-speed expansion ports 510, and a low speed interface 512 connecting to low speed bus 514 and storage device 506. Each of the components 502, 504, 506, 508, 510, and 512, are interconnected using various busses, and may be mounted on a common motherboard or in other manners as appropriate. The processor 502 can process instructions for execution within the computing device 500, including instructions stored in the memory 504 or on the storage device 506 to display graphical information for a GUI on an external input/output device, such as display 516 coupled to high speed interface 508. In other implementations, multiple processors and/or multiple buses may be used, as appropriate, along with multiple memories and types of memory. Also, multiple computing devices 500 may be connected, with each device providing portions of the necessary operations, e.g., as a server bank, a group of blade servers, or a multi-processor system.

The memory 504 stores information within the computing device 500. In one implementation, the memory 504 is a computer-readable medium. In one implementation, the memory 504 is a volatile memory unit or units. In another implementation, the memory 504 is a non-volatile memory unit or units.

The storage device 506 is capable of providing mass storage for the computing device 500. In one implementation, the storage device 506 is a computer-readable medium. In various different implementations, the storage device 506 may be a floppy disk device, a hard disk device, an optical disk device, or a tape device, a flash memory or other similar solid-state memory device, or an array of devices, including devices in a storage area network or other configurations. In one implementation, a computer program product is tangibly embodied in an information carrier. The computer program product contains instructions that, when executed, perform one or more methods, such as those described above. The information carrier is a computer- or machine-readable medium, such as the memory 504, the storage device 506, or memory on processor 502.

The high-speed controller 508 manages bandwidth-intensive operations for the computing device 500, while the low speed controller 512 manages lower bandwidth-intensive operations. Such allocation of duties is exemplary only. In one implementation, the high-speed controller 508 is coupled to memory 504, display 516, e.g., through a graphics processor or accelerator, and to high-speed expansion ports 510, which may accept various expansion cards (not shown). In the implementation, low-speed controller 512 is coupled to storage device 506 and low-speed expansion port 514. The low-speed expansion port, which may include various communication ports, e.g., USB, Bluetooth, Ethernet, wireless Ethernet, may be coupled to one or more input/output devices, such as a keyboard, a pointing device, a scanner, or a networking device such as a switch or router, e.g., through a network adapter.

The computing device 500 may be implemented in a number of different forms, as shown in the figure. For example, it may be implemented as a standard server 520, or multiple times in a group of such servers. It may also be implemented as part of a rack server system 524. In addition, it may be implemented in a personal computer such as a laptop computer 522. Alternatively, components from computing device 500 may be combined with other components in a mobile device (not shown), such as device 550. Each of such devices may contain one or more of computing device 500, 550, and an entire system may be made up of multiple computing devices 500, 550 communicating with each other.

Computing device 550 includes a processor 552, memory 564, an input/output device such as a display 554, a communication interface 566, and a transceiver 568, among other components. The device 550 may also be provided with a storage device, such as a microdrive or other device, to provide additional storage. Each of the components 550, 552, 564, 554, 566, and 568, are interconnected using various buses, and several of the components may be mounted on a common motherboard or in other manners as appropriate.

The processor 552 can process instructions for execution within the computing device 550, including instructions stored in the memory 564. The processor may also include separate analog and digital processors. The processor may provide, for example, for coordination of the other components of the device 550, such as control of user interfaces, applications run by device 550, and wireless communication by device 550.

Processor 552 may communicate with a user through control interface 558 and display interface 556 coupled to a display 554. The display 554 may be, for example, a TFT LCD display or an OLED display, or other appropriate display technology. The display interface 556 may include appropriate circuitry for driving the display 554 to present graphical and other information to a user. The control interface 558 may receive commands from a user and convert them for submission to the processor 552. In addition, an external interface 562 may be provided in communication with processor 552, so as to enable near area communication of device 550 with other devices. External interface 562 may provide, for example, for wired communication, e.g., via a docking procedure, or for wireless communication, e.g., via Bluetooth or other such technologies.

The memory 564 stores information within the computing device 550. In one implementation, the memory 564 is a computer-readable medium. In one implementation, the memory 564 is a volatile memory unit or units. In another implementation, the memory 564 is a non-volatile memory unit or units. Expansion memory 574 may also be provided and connected to device 550 through expansion interface 572, which may include, for example, a SIMM card interface. Such expansion memory 574 may provide extra storage space for device 550, or may also store applications or other information for device 550. Specifically, expansion memory 574 may include instructions to carry out or supplement the processes described above, and may include secure information also. Thus, for example, expansion memory 574 may be provided as a security module for device 550, and may be programmed with instructions that permit secure use of device 550. In addition, secure applications may be provided via the SIMM cards, along with additional information, such as placing identifying information on the SIMM card in a non-hackable manner.

The memory may include for example, flash memory and/or MRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 564, expansion memory 574, or memory on processor 552.

Device 550 may communicate wirelessly through communication interface 566, which may include digital signal processing circuitry where necessary. Communication interface 566 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 568. In addition, short-range communication may occur, such as using a Bluetooth, WiFi, or other such transceiver (not shown). In addition, GPS receiver module 570 may provide additional wireless data to device 550, which may be used as appropriate by applications running on device 550.

Device 550 may also communicate audibly using audio codec 560, which may receive spoken information from a user and convert it to usable digital information. Audio codec 560 may likewise generate audible sound for a user, such as through a speaker, e.g., in a handset of device 550. Such sound may include sound from voice telephone calls, may include recorded sound, e.g., voice messages, music files, etc., and may also include sound generated by applications operating on device 550.

The computing device 550 may be implemented in a number of different forms, as shown in the figure. For example, it may be implemented as a cellular telephone 580. It may also be implemented as part of a smartphone 582, personal digital assistant, or other similar mobile device.

Various implementations of the systems and techniques described here can be realized in digital electronic circuitry, integrated circuitry, specially designed ASICs, computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs, also known as programs, software, software applications or code, include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device, e.g., magnetic discs, optical disks, memory, Programmable Logic Devices (PLDs) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The systems and techniques described here can be implemented in a computing system that includes a back-end component, e.g., as a data server, or that includes a middleware component such as an application server, or that includes a front-end component such as a client computer having a graphical user interface or a Web browser through which a user can interact with an implementation of the systems and techniques described here, or any combination of such back-end, middleware, or front-end components. The components of the system can be interconnected by any form or medium of digital data communication such as, a communication network. Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

In addition, certain data may be treated in one or more ways before it is stored or used, so that personally identifiable information is removed. For example, in some embodiments, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over what information is collected about the user, how that information is used, and what information is provided to the user.

A number of embodiments have been described. Nevertheless, it will be understood that various modifications may be made without departing from the spirit and scope of the invention. Accordingly, other embodiments are within the scope of the following claims. While this specification contains many specific implementation details, these should not be construed as limitations on the scope of what may be claimed, but rather as descriptions of features that may be specific to particular embodiments. Certain features that are described in this specification in the context of separate embodiments can also be implemented in combination in a single embodiment.

Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, some processes depicted in the accompanying figures do not necessarily require the particular order shown, or sequential order, to achieve desirable results.

The invention claimed is:

1. A computer-implemented method comprising:
  generating a training dataset comprising a plurality of first distinct data sequences derived from information about healthcare transactions and providers for a set of patients;
  determining a first set of features from the plurality of first distinct data sequences in the training dataset, wherein the first set of features is determined based on commonalities among parameters in the plurality of first distinct data sequences from which the first set of features is determined;
  generating a predictive model by:
    training a first neural network to generate output vector data sets in response to processing inputs corresponding to the first set of features through a plurality of layers of the first neural network;
    training a second neural network to generate an indication of undiagnosed conditions of the set of patients (i) using the output vector data sets and (ii) by processing inputs corresponding to the first set of features, wherein the trained second neural network represents the predictive model;
    determining a second set of features from at least some of the plurality of first distinct data sequences for scoring the predictive model;
    in response to determining the second set of features, generating a first confidence score by providing the second set of features as input to the predictive model, wherein the first confidence score represents an accuracy of the predictive model to predict future undiagnosed health conditions of patients;
    comparing the first confidence score to a threshold value to evaluate the accuracy of the predictive model;
    in response to determining the first confidence score satisfies the threshold value, providing the predictive model for output;
  generating, by the predictive model, a prediction of a future undiagnosed health condition of a patient based on inferences determined from the predictive model and a third set of features determined from a plurality of second distinct data sequences, wherein the plurality of first distinct data sequences are different from the plurality of second distinct data sequences;
  generating, from the predictive model, an output that comprises the prediction of the future undiagnosed health condition of the patient;
  in response to generating the output, identifying one or more clinical trials and corresponding site locations that execute trial programs for evaluating medical options for treating the predicted future undiagnosed health condition of the patient;
  generating data that links medical information of the patient to information of the one or more identified clinical trials; and
  providing the linked data for output.

2. The computer-implemented method of claim 1, wherein generating the prediction of the future undiagnosed health condition of the patient further comprises:
  determining, by the predictive model, a second confidence score that represents a confidence in an accuracy of the future undiagnosed health condition of the patient in response to processing the third set of features corresponding to the patient through one or more layers of the predictive model.

3. The computer-implemented method of claim 2, wherein generating the predictive model comprises:
  providing a first data sequence and a second data sequence of the plurality of first distinct data sequences as inputs to a first layer of the first neural network, wherein the first data sequence is different from the second data sequence and each of the first data sequence and the second data sequence correspond to a respective set of features; and
  training the second neural network using the sets of features in response to processing the first data sequence and the second data sequence through the first neural network.

4. The computer-implemented method of claim 3, wherein the predictive model determines the second confidence score that represents the confidence in the accuracy of the future undiagnosed health condition of the patient based on training inferences computed when the predictive model is trained using at least the first data sequence and the second data sequence of the plurality of first distinct data sequences.

5. The computer-implemented method of claim 4, further comprising:
  determining a third data sequence based on the information about the healthcare transactions and the providers for the set of patients, wherein the third data sequence represents training data that describes patient specific information; and
  generating the predictive model at least by processing each of the first, second, and third data sequence of the plurality of first distinct data sequences through the one or more layers of the first neural network.

6. The computer-implemented method of claim 5, wherein:
  the first data sequence comprises data describing procedures, products, or diagnoses and is formatted for processing through the one or more layers of the first neural network;
  the second data sequence comprises data describing healthcare provider specialties and is formatted for processing through the one or more layers of the first neural network; and
  the third data sequence comprises data describing patient demographics and is formatted for processing through the one or more layers of the first neural network.

7. The computer-implemented method of claim 6, further comprising:
encoding, as a vector, at least one of a procedure, a product, and a diagnosis in the first data sequence; and
obtaining an encoding rule associated with the vector by using the second neural network to learn inferences based on analysis of data corresponding to the training dataset.

8. The computer-implemented method of claim 1, wherein the predictive model is a trained neural network model configured to identify latent variables in patient scoring data derived from the information about the healthcare transactions and the providers for the set of patients.

9. The computer-implemented method of claim 1, wherein:
the future undiagnosed health condition of the patient reflects at least one of (i) a current healthcare condition or (ii) a prospective healthcare condition, that is not yet diagnosed for the patient; and
the output: (i) identifies a particular disease that currently affects the patient, or (ii) identifies whether the patient is at risk for contracting a particular disease.

10. The computer-implemented method of claim 9, wherein the method further comprises:
identifying a healthcare provider for treating the particular disease;
linking first data for the patient to second data for the healthcare provider; and
providing the indication using linked data for the patient and the healthcare provider.

11. The computer-implemented method of claim 9, wherein the method further comprises:
identifying a healthcare provider for treating the particular disease.

12. The computer-implemented method of claim 1, wherein generating the predictive model further comprises:
generating, iteratively, feedback data that comprises at least some of the output vector data sets output by the first neural network; and
providing the generated feedback data to be used as the training dataset for generating the predictive model.

13. The computer-implemented method of claim 1, wherein generating the training dataset comprises:
generating the training dataset from data for a subset of patients that each have the same healthcare condition.

14. The computer-implemented method of claim 1, wherein the first and second neural networks are implemented on a hardware circuit of a predictive system that includes the predictive model and the computer-implemented method further comprises:
generating, at the predictive system, the plurality of first distinct data sequences by sequencing a portion of the information from the training dataset for each of the healthcare transactions and the providers for the set of patients;
generating a plurality of vector datasets from the plurality of first distinct data sequences that describes the set of patients, wherein (i) a first vector dataset describes healthcare transactions for the set of patients, (ii) a second vector dataset describes healthcare providers that engage in the healthcare transactions for treating the set of patients, and (iii) a third vector dataset describes demographics for each patient in the set of patients; and
generating, by the predictive system, a set of computing rules based on the plurality of vector datasets implemented on the hardware circuit.

15. A system, comprising:
one or more processing devices; and
one or more non-transitory machine-readable storage devices storing instructions that are executable by the one or more processing devices to cause performance of operations comprising:
generating a training dataset comprising a plurality of distinct data sequences derived from information about healthcare transactions and providers for a set of patients;
determining a first set of features from the plurality of first distinct data sequences in the training dataset, wherein the first set of features is determined based on commonalities among parameters in the plurality of first distinct data sequences from which the first set of features is determined;
generating a predictive model by:
training a first neural network to generate output vector data sets in response to processing inputs corresponding to the first set of features through a plurality of layers of the first neural network;
training a second neural network to generate an indication of undiagnosed conditions of the set of patients (i) using the output vector data sets and (ii) by processing inputs corresponding to the first set of features, wherein the trained second neural network represents the predictive model;
determining a second set of features from at least some of the plurality of first distinct data sequences for scoring the predictive model;
in response to determining the second set of features, generating a first confidence score by providing the second set of features as input to the predictive model, wherein the first confidence score represents an accuracy of the predictive model to predict future undiagnosed health conditions of patients;
comparing the first confidence score to a threshold value to evaluate the accuracy of the predictive model;
in response to determining the first confidence score satisfies the threshold value, providing the predictive model for output;
generating, by the predictive model, a prediction of a future undiagnosed health condition of a patient based on inferences determined from the predictive model and a third set of features determined from a plurality of second distinct data sequences, wherein the plurality of first distinct data sequences are different from the plurality of second distinct data sequences;
generating, from the predictive model, an output that comprises the prediction of the future undiagnosed health condition of the patient;
in response to generating the output, identifying one or more clinical trials and corresponding site locations that execute trial programs for evaluating medical options for treating the predicted future undiagnosed health condition of the patient;
generating data that links medical information of the patient to information of the one or more identified clinical trials; and
providing the linked data for output.

16. The system of claim 15, wherein generating the prediction of the future undiagnosed health condition of the patient further comprises:

determining, by the predictive model, a second confidence score that represents a confidence in an accuracy of the future undiagnosed health condition of the patient in response to processing the third set of features corresponding to the patient through one or more layers of the predictive model.

17. The system of claim 16, wherein generating the predictive model comprises:
providing a first data sequence and a second data sequence of the plurality of first distinct data sequences as inputs to a first layer of the first neural network, wherein the first data sequence is different from the second data sequence and each of the first data sequence and the second data sequence correspond to a respective set of features; and
training the second neural network using the respective sets of features in response to processing the first data sequence and the second data sequence through the first neural network.

18. The system of claim 17, wherein the predictive model determines the second confidence score that represents the confidence in the accuracy of the future undiagnosed health condition of the patient based on training inferences computed when the predictive model is trained using at least the first data sequence and the second data sequence of the plurality of first distinct data sequences.

19. The system of claim 18, wherein the operations further comprise:
determining a third data sequence based on the information about the healthcare transactions and the providers for the set of patients, wherein the third data sequence represents training data that describes patient specific information; and
generating the predictive model at least by processing each of the first, second, and third data sequence of the plurality of first distinct data sequences through the one or more layers of the first neural network.

20. The system of claim 15, wherein the predictive model is a trained neural network model configured to identify latent variables in patient scoring data derived from the information about the healthcare transactions and the providers for the set of patients.

21. One or more non-transitory machine-readable storage devices storing instructions that are executable by one or more processing devices to cause performance of operations comprising:
generating a training dataset comprising a plurality of distinct data sequences derived from information about healthcare transactions and providers for a set of patients;
determining a first set of features from the plurality of first distinct data sequences in the training dataset, wherein the first set of features is determined based on commonalities among parameters in the plurality of first distinct data sequences from which the first set of features is determined;

generating a predictive model by:
training a first neural network to generate output vector data sets in response to processing inputs corresponding to the first set of features through a plurality of layers of the first neural network;
training a second neural network to generate an indication of undiagnosed conditions of the set of patients (i) using the output vector data sets and (ii) by processing inputs corresponding to the first set of features, wherein the trained second neural network represents the predictive model;
determining a second set of features from at least some of the plurality of first distinct data sequences for scoring the predictive model;
in response to determining the second set of features, generating a first confidence score by providing the second set of features as input to the predictive model, wherein the first confidence score represents an accuracy of the predictive model to predict future undiagnosed health conditions of patients;
comparing the first confidence score to a threshold value to evaluate the accuracy of the predictive model;
in response to determining the first confidence score satisfies the threshold value, providing the predictive model for output;
generating, by the predictive model, a prediction of a future undiagnosed health condition of a patient based on inferences determined from the predictive model and a third set of features determined from a plurality of second distinct data sequences, wherein the plurality of first distinct data sequences are different from the plurality of second distinct data sequences;
generating, from the predictive model, an output that comprises the prediction of the future undiagnosed health condition of the patient;
in response to generating the output, identifying one or more clinical trials and corresponding site locations that execute trial programs for evaluating medical options for treating the predicted future undiagnosed health condition of the patient;
generating data that links medical information of the patient to information of the one or more identified clinical trials; and
providing the linked data for output.

22. The computer-implemented method of claim 14, wherein the method further comprises:
applying, by the first neural network and the second neural network implemented on the hardware circuit, a machine-learning algorithm to the plurality of vector datasets to: i) train the first and second neural networks and ii) generate the predictive model.

* * * * *